United States Patent [19]

Flashner et al.

[11] 4,071,408
[45] Jan. 31, 1978

[54] NEURAMINIDASE

[75] Inventors: Michael Flashner, Syracuse; Stuart W. Tanenbaum, Manlius, both of N.Y.

[73] Assignee: Research Corporation, New York, N.Y.

[21] Appl. No.: 735,521

[22] Filed: Nov. 1, 1976

[51] Int. Cl.$^2$ ............................................. C12D 13/10
[52] U.S. Cl. ........................................ 195/62; 195/65; 195/114; 195/100
[58] Field of Search ................. 195/62, 65, 66 R, 100, 195/114

[56] References Cited

U.S. PATENT DOCUMENTS 3,259,550  7/1966  Stacey et al. ..................... 195/66 R

OTHER PUBLICATIONS

Chemical Abstracts, vol. 85, 121816j, 1976 abstract of Japan Kokai 32,786 Mar. 19, 1976.
Howe et al., Archives of Biochemistry and Biophysics 95, 512–520 (1961).

Primary Examiner—Lionel M. Shapiro
Attorney, Agent, or Firm—Cooper, Dunham, Clark, Griffin & Moran

[57] ABSTRACT

Extracellular neuraminidase (NANAase) is produced by the microorganism *Arthrobacter sialophilum* sp. nov. The enzyme is induced from this microorganism by a variety of glycoproteins. The preferred enzyme inducer is a hot water extract of edible bird's nest which has been mildly acid-treated. The microorganisms, after aerobic growth in complete medium of relatively simple composition, are harvested, washed, salt-shocked, and induced in mineral salts solution which leads to facile enzyme induction. The produced NANAase is purified by ammonium sulfate fractionation, DEAE cellulose chromatography, gel filtration and ultrafiltration. The enzyme can further be readily crystallized from concentrated solutions. Disc gel electrophoresis at both acidic and basic pH's showed a major protein band. The predominant protein contained NANAase activity. The NANAase has an apparent molecular weight of 87,000 daltons. The purified enzyme has a pH optimum of 5–6, an apparent $K_m$ of 2.08 mg/ml for Collocalia mucoid and $3.3 \times 10^{-3}$ M for N-acetylneuraminlactose and is insensitive to Ca++ ions and EDTA. Linkage specificity studies using N-acetylneuraminlactose and colominic acid indicated that the NANAase hydrolyzes ($\alpha$, 2-3), ($\alpha$, 2-6) or ($\alpha$, 2-8) linkages. The above-identified microorganism produces about 5 mg of NANAase/liter of induction medium and is an excellent source for the preparation of relatively large quantities of homogeneous NANAase.

13 Claims, No Drawings

NEURAMINIDASE

This invention relates to neuraminidases. In one embodiment, this invention is directed to the production of neuraminidases. In another embodiment, this invention is directed to a neuraminidase prepared from a specific microorganism. In another embodiment, this invention is directed to materials useful in combination with a special microorganism or variant or derivative thereof for the production of extracellular neuraminidase.

Neuraminidases have been employed for the alteration and/or modification of carbohydrates and cell surfaces, have been used for the treatment or regression of solid tumors and are useful in immunological and birth control investigations and applications. Other uses of neuraminidases are known; see, for example, U.S. Pat. 3,259,550. The disclosures of this patent, insofar as the disclosures relate to the invention disclosed and claimed herein, are incorporated and made part of this disclosure.

The microorganisms or bacterial sources presently employed for the production of neuraminidases are human pathogens. These microorganisms or sources require relatively complex growth media and conditions and yield only small amounts of the desired enzyme, neuraminidase. In addition, the resulting produced neuraminidases are usually contaminated with glycohydrolases, proteases, phospholipases and hemolysins. These contaminants are difficult to remove from the produced neuraminidase.

It is an object of this invention to provide a method for the production of neuraminidase from a microorganism not known or generally considered to be a human pathogen.

It is another object of this invention to provide a method for the production of neuraminidase in high yields.

It is still another object of this invention to provide a special neuraminidase, particularly a neuraminidase of improved purity and/or homogeneity.

Still another object of this invention is to provide materials useful for the production of neuraminidase in relatively high yields from a special microorganism capable of producing extracellular neuraminidase.

How these and other objects of this invention are achieved will become apparent in the light of the accompanying disclosure. In at least one embodiment in the practices of this invention, at least one of the foregoing objects will be achieved.

It has been discovered that the microorganism *Arthrobacter sialophilum* sp. nov. or variant or derivative thereof is capable of producing substantially large quantities of neuraminidase, for example, approximately 100 times more enzyme than is produced by the microorganism *Clostridium perfringens*, a microorganism used by commercial suppliers for the production and isolation of this enzyme.

Neuraminidase (NANAase) E.C.3.2.1.18 is prepared in accordance with the practices of this invention by growing the microorganism *A. sialophilum* sp. nov. or variant or derivative thereof in a medium containing tryptone-yeast extract, followed by induction of the harvested cells for neuraminidase.

Neuraminidase is induced from the microorganism by a variety of glycoproteins and low molecular weight glycopeptides having a molecular weight in the range about 500–50,000, preferably in the range 1,000–10,000, more or less. It has been observed that the enzyme is not produced in the absence of inducers or in the presence of chloramphenicol or chlortetracycline. The materials or inducers useful in the practices of this invention include a variety of glycoproteins containing sialic acid. It is preferred in the practices of this invention to employ as the enzyme inducer a hot water extract of edible bird's nest, a Collocalia mucoid. The enzyme NANAase was purified 70-fold by ammonium sulfate fractionation, DEAE cellulose chromatography and gel filtration. Disc gel electrophoresis at both acidic pH and basic pH revealed a major protein band with several minor contaminants. The predominant protein, however, contained all the NANAase activity. The resulting produced NANAase has a molecular weight of 87,000 daltons as judged by gel filtration chromatography on a calibrated Sephadex column. The purified enzyme has a pH optimum of 5–6, an apparent $K_m$ of about 2.08 mg/ml for Collocalia mucoid and $3.3 \times 10^{-3}$ M for N-acetylneuraminlactose and is insensitive to both $Ca^{++}$ ions and EDTA. Linkage specificity studies using N-acetylneuraminlactose and colominic acid indicated that NANAase can hydrolyze $(\alpha, 2-3)$, $(\alpha, 2-6)$ or $(\alpha, 2-8)$ linkages.

Of particular interest from a commercial point of view, in addition to the high yields of NANAase obtainable from the microorganism employed in the practices of this invention, are the other desirable properties of this microorganism which include non-pathogenicity, rapid aerobic growth in defined media, high enzyme inducibility without the appreciable production of other glycohydrolases and proteases and the relative ease of recovery and purification of the resulting produced NANAase.

Following is a detailed description of the practices of this invention.

The reagents employed in the procedures set forth hereinbelow include Sephadex G-150 or G-200 (Pharmacia), DEAE-cellulose (Reeve Angel), N-acetylneuraminlactose (Beef colostrum), N-acetylneuraminic acid, fetuin and submaxillary mucin obtained from Sigma Chemical Co. and colominic acid obtained from Calbiochem. All other chemicals were of reagent-grade quality.

Glycoprotein preparations. Crude "edible bird's nest" was ground to a fine powder and soaked in tap water at a final concentration of 4% (w/v). The suspension was refluxed for 5 hours, followed by filtration, and used per se. "Acid-treated bird's nest" resulted from bringing the bird's nest to 0.05N with $H_2SO_4$, followed by heating for 1.5 hours at 80° C. It should be noted that the temperature and pH are critical for optimum induction. After cooling, the pH was adjusted to 7.0 with saturated $Ba(OH)_2$, and the precipitated $BaSO_4$ was removed by centrifugation. Collocalia mucoid was made essentially as described by Howe, et al (Howe, C., L. T. Lee, and H. M. Rose. 1961. Collocalia mucoid: a substrate for myxovirus neuraminidase. Arch. Biochem. Biophys. 95:512–520). In this preparation, the crude bird's nest percolate was treated for 3 hours at 60° C., followed by dialysis against glass distilled water and lyophilization.

Culture media. Complete medium "TYE" was composed of 1% (w/v) bacto-tryptone-0.50% (w/v) yeast extract. Pure cultures were maintained on TYE agar. Minimal medium was the "M-9" solution detailed by Adams (Adams, M. H. 1959. Bacteriophages, p. 446. Interscience Publishers, New York) modified to contain sodium chloride. The composition is as follows: Na$_2$HPO$_4$, 5.8 g; KH$_2$PO$_4$, 3.0 g; NaCl, 0.5 g; NH$_4$Cl, 1.0 g; MgSO$_4$, 0.12 g; dissolved per 1 of deionized water. For certain induction experiments, two to ten-fold concentrations of M-9 designated "2× to 10×" were utilized. The organism was initially grown on a rotatory shaker (150 rpm) in TYE for 15 hours at 30° C. The collected cells were washed with sterile 0.90% NaCl, resuspended in an appropriate multiple of M-9 medium at a final concentration of around 10$^{10}$ cells/ml, and stored in the cold. In all experiments, enzyme induction was then carried out in 2× M-9 medium by diluting the salt-shocked cells to a final cell concentration of around 3 × 10$^9$ cells/ml with the appropriate inducer preparation.

Neuraminidase and related assays. The activity of enzyme preparations was determined as follows: A reaction mixture containing 40 μmols of citrate-phosphate buffer, pH 6.0, 1.0 mg of Collocalia mucoid and the enzyme fraction in a final volume of 0.50 ml was incubated at 37° C. Aliquots of 0.20 ml were withdrawn at 5 and 10 minutes, and the N-acetylneuraminic acid determined. In all experiments, zero time points were run for each extract. A unit of enzyme activity is defined as that amount which releases 1 μmol of N-acetylneuraminic acid per minute from the mucoid preparation, under conditions of the standard assay given above. Specific activity is expressed as units/mg of protein. Protein was determined with crystalline bovine serum albumin as standard. N-acetylneuraminate pyruvatelyase assays were carried out.

DNA isolation and GC mol % analysis. The final preparation had a 260/280 ratio of 2.17. The GC mol % was determined by buoyant density experiments with a Beckman model E ultracentrifuge equipped with a photoelectric scanner and multiplexer. Bacteriophage PM2 DNA (buoyant density 1.696) was used as the marker. This secondary standard had previously been calibrated against *M. lysodeikticus* DNA. Corrected buoyant densities for *A. sialophilum* were calculated.

Electrophoresis. Disc gel electrophoresis was carried out at 4° C. for 120 minutes in either the Tris-glycine or the acetic acid-β-alanine buffer systems in 6.0% polyacrylamide gel (Gabriel, O. 1971. Analytical disc gel electrophoresis, p. 565–578. In W. B. Jakoby (ed.), Methods in Enzymol., vol. 22. Academic Press, New York). The gels were soaked in 12.5% TCA for 30 minutes with agitation and stained with 0.050% Coomassie brilliant blue in 12.5% TCA for 1 hour at 80° C. The gels were destained by soaking in 10% TCA for 48 hours in the dark. Although difficulties in staining bacterial neuraminidases have been reported (Geisow, M. J. 1975. An improved method for purifying sialidase. Biochem. J. 151:181–183; Hatton, M. W. C., and E. Regoeczi. 1973. A simple method for the purification of commercial neuraminidase free from proteases. Biochim. Biophys. Acta 327:114–120), the procedure described above gave sharp blue bands with as little as 10 μg neuraminidase. For determination of neuraminidase activity, unstained replicate disc gels were cut into sections, each 2.0 mm thick, using an apparatus purchased from Biorad. Each section was then incubated overnight in 0.010 M citrate-phosphate buffer, pH 6.0, and neuraminidase activity was determined by incubating aliquots in Collocalia mucoid for 60 minutes at 37° C. Alternatively, the gels were stained with MPN (Tuppy, H., and S. Palese. 1969. A chromogenic substrate for the investigation of neuraminidase. FEBS Letts. 3:72–75), methoxyphenyl-N-acetyl-α-neuraminate.

Molecular weight determinations. The molecular weight of neuraminidase was estimated by the method of Andrews (Andrews, P. 1965. The gel filtration behavior of proteins related to their molecular weights over a wide range. Biochem. J. 96:595–606). A column of Sephadex G-150 (1.5 × 90 cm) was equilibrated with 0.010 M citrate-phosphate buffer, pH 6.0, and run at a flow rate of 12 ml/hour. Calibration standards included γ-globulin, bovine serum albumin, chymotrypsinogen, myoglobin and cytochrome C. These determinations were made at 4° C.

Growth characteristics of *A. sialophilum*. As shown in Table 1, growth of the microorganism took place on a variety of glycoproteins which were used as sole carbon and nitrogen sources. This accords with the previously reported broad versatility of Arthrobacter catabolic enzymes. Although Collocalia mucoid was initially used for the selection of *A. sialophilum*, the best neuraminidase production, in terms of enzyme activity, was obtained with the crude bird's nest extract. The other sialoproteins were intermediate stimulators of enzyme activity. The contrast between Collocalia mucoid and the crude undialyzed preparation, insofar as neuraminidase production, may reflect the removal of lower molecular weight, complex inducer materials.

TABLE 1

Activity of Neuraminidase from Cells Grown with Glycoproteins as Sole Carbon and Nitrogen Source

| Glycoprotein | Activity (units/ml) | Specific Activity (units/mg protein) |
|---|---|---|
| Crude bird's nest extract | 0.132 | 0.349 |
| Collocalia mucoid | 0.004 | 0.025 |
| Submaxillary mucin | 0.078 | 0.243 |
| Fetuin | 0.036 | 0.157 |

Cells were grown for 22 hours in 10 ml. of M-9 medium containing the appropriate glycoprotein at a final concentration of 0.050%, centrifuged, and the activity of neuraminidase in the growth filtrate was determined as given hereinabove.

When overnight cultures of *A. sialophilum* were grown in TYE, washed with saline, and resuspended in 2x M-9 mixture, it was found, see Table 2, in contrast to the above, that only crude bird's nest extract or its transformation products acted as inducers. When, however, such cells were exposed for 2 hours to 10× M-9 at 4° C., not only was stimulation of enzyme activity enhanced with the foregoing glycoprotein preparations, but fetuin and submaxillary mucin also induced enzyme formation. It should be noted, in both experiments, that the actual induction process took place in 2× M-9. Therefore, *A. sialophilum* cells were salt-shocked with 10× M-9 prior to inductions. Although it has been reported that N-acetylneuraminic acid or N-acetylmannosamine are good inducers for bacterial neuraminidase, under the protocols stated these monosaccharides were not effective with *A. sialophilum*. The apparent high specific activity with N-acetylneuraminic acid in 10×-treated cells reflects, because of poor total activity, a low measurable protein concentration rather than an amplified enzyme synthesis. No neuraminidase activity was detected in non-induced cells or in the growth filtrate obtained from cells grown in TYE.

TABLE 2

Stimulation of neuraminidase activity in replacement media

| Addition | Concentration (mg/ml) | 2 × M-9[a] Activity (units/ml) | Specific Activity (units/mg protein) | Concentration (mg/ml) | 10 × M-[b] Activity (units/ml) | Specific Activity (units/mg protein) |
|---|---|---|---|---|---|---|
| Crude bird's nest extract | 0.16 | 0.03 | 0.22 | 1.20 | 0.09 | 0.11 |
| Collocalia mucoid | 0.16 | 0.03 | 0.20 | 0.40 | 0.04 | 0.21 |
| Acid-treated bird's nest | 0.16 | 0.06 | 0.48 | 0.53 | 0.29 | 1.25 |
| Fetuin | 0.16 | 0.0 | 0.0 | 0.40 | 0.56 | 0.04 |
| Submaxillary mucin | 0.03 | 0.0 | 0.0 | 0.40 | 0.29 | 0.11 |
| N-acetylneuraminic acid | 0.16 | 0.0 | 0.0 | 4.0 | 0.05 | 3.73 |
| N-acetylmannosamine | 0.16 | 0.0 | 0.0 | 4.0 | 0.01 | 0.23 |
| Control | — | 0.0 | 0.0 | — | 0.0 | 0.0 |

[a] Cells grown 18 hr in TYE, washed with 0.9% NaCl, resuspended in 2 × M-9 and stored at 4° C. for 18 hr. Enzyme induction was carried out with the indicated substrate for 6 hr at 30° C. in 2 × M-9 at a cell count of 3.3 × 10$^9$ cells/ml. Neuraminidase activity measured as described in Materials and Methods.
[b] Cells grown 15 hr in TYE, washed with 0.90% NaCl, resuspended in 10 × M-9 and stored at 40° C. for 18 hr. Enzyme induction was carried out with the indicated substrate for 10 hr at 30° C. in 2 × M-9 at a cell count of 1.4 × 10$^9$ cells/ml.

Replacement medium filtrates obtained from cells induced with acid-treated bird's nest were tested for presence of other glycohydrolases with appropriate α- and β-p-nitrophenylketosides. Neither α-mannosidase, α- and β-galactosidase, α- and β-glucosidase, α- and β-fucosidase, N-acetyl-β-galactosamidase, nor N-acetyl-α-glucosamidase activities were detected.

That the above observations reflect an actual specific neuraminidase induction was bolstered by a series of experiments in which replacement cultures with acid-treated bird's nest extract were supplemented with antibiotics. As seen in Table 3, inhibitors of protein synthesis, such as chloramphenicol or chlortetracycline, completely suppressed the appearance of enzyme activity, while penicillin and neomycin had no inhibitory effect. It was again observed that no neuraminidase activity could be detected in the unsupplemented salts medium. These data show that the accumulation of neuraminidase by this microorganism reflects de novo protein synthesis rather than the release of preformed enzyme.

The inability to observe neuraminidase activity in cells which had been treated with inhibitors of protein synthesis suggests the absence of any significant pool of preformed enzyme. Measurements of the level of intra- and extracellular levels of neuraminidase were made on cells which were induced with the acid-treated bird's nest. Cells were collected by centrifugation, washed with 0.9% NaCl, suspended in 0.10 M citrate phosphate buffer, pH 6.0, and sonicated. Cell debris was removed by centrifugation, and neuraminidase activity determined in the supernatant. Under this protocol, only 0.051 total units of enzyme activity could be detected within the cells, whereas a total of 11.5 units was found in the induction filtrate. This small amount of intracellular enzyme is negligible compared to that found extracellularly and could easily represent absorbed enzyme rather than truly intracellular material. Corollary experiments indicated that N-acetylneuraminate pyruvate-lyase, while present in low activity within cell-free extracts, was not found in the extracellular induction medium.

TABLE 3

Induction of Neuraminidase Activity in the Presence of Antibiotics

| Compound Added | Activity (units/ml) | Specific Activity (units/mg protein) |
|---|---|---|
| None | 0.0 | 0.0 |
| Acid-treated bird's nest (ATBN) | 0.265 | 0.848 |
| ATBN + chloramphenicol | 0.0 | 0.0 |
| ATBN + chlortetracycline | 0.0 | 0.0 |
| ATBN + neomycin | 0.292 | 0.925 |
| ATBN + penicillin G | 0.300 | 0.755 |

Cells were grown as described in footnote b, Table 2 with acid-treated bird's nest as the inducer. In all cases the antibiotic was added to the inductonmedium at a final concentration of 50 μ/ml.

Acid treatment of bird's nest extract stimulates its action both for total and specific enzyme activity. The greatest increase in neuraminidase activity occurred within the first 30 minutes of acid treatment, followed by a small linear increase. Thin layer chromatography of the 0.05N acid-treated extract revealed a new Ehrlich positive spot which had not been observed in the original extract. Fractionation of the acid-treated bird's nest into different molecular weight components revealed that this preparation contained several different inducing materials; the most active had molecular weights in the range 1,000–10,000 daltons. From these experiments, a standard time of acid treatment of 1.5 hours was chosen for subsequent work with this inducer preparation. It is understood that the actual inducer or inducers are most likely glycopeptides or protein-associated saccharides in nature. The activity/ml of neuraminidase was biphasic with a rapid initial linear phase that became significantly slower at about 0.25 mg/ml acid-treated bird's nest. In contrast, the specific activity of the enzyme increased very rapidly through the initial linear phase of activity, reaching a maximum of 1.36 units/mg of protein, and then decreased with increased accumulation of activity. As a compromise between changes in specific activity and total activities, a final concentration of 0.40 mg/ml was chosen as standard. The activity of this inducer concentration versus the number of A. sialophilum cells was examined. Neuraminidase activity was manifested at an exponential rate, reaching a maximum at 3 × 10$^9$ cells/ml, before decreasing. Therefore, large scale preparations of enzyme utilized this cell density.

Parameters of enzyme induction. Induction of neuraminidase by A. sialophilum was enhanced by pretreatment with high M-9 salt medium. A series of experiments was carried out to quantitate this effect. Exposure of cells to 8× M-9 provided maximal enzyme formation. Aliquots removed from these experiments gave, within experimental error, identical cell counts when plated on TYE. Wet mounts of cells examined at each of these salt concentrations were totally coccoid in form.

This salt-shocking effect, presumably, is due to some undetermined permeability consequence.

In order to examine the relationship of *A. sialophilum* multiplication to enzyme induction, the synthesis of neuraminidase versus cell count was carried out. The plotted results showed a curve characterized by a significant lag of approximately 6 hours, followed by exponential growth, which gave a generation time of 3.25 hours. During the lag phase, enzyme synthesis was linear and leveled off as the microorganism entered the exponential phase. Also, the specific activity of the extracellular neuraminidase paralleled enzyme activity, reaching a maximum of 1.10 units/mg of protein.

Purification of *A. sialophilum* neuraminidase. The procedures used in purifying neuraminidase are summarized in Table 4.

TABLE 4

Purification of Neuraminidase from *Arthrobacter Sialophilum*

| Preparation | Volume (ml) | Protein (mg) | Protein (units) | Specific Activity $\left(\frac{\text{units}}{\text{mg protein}}\right)$ | Yield % |
|---|---|---|---|---|---|
| Induction filtrate (I) | 4040 | 1959 | 824 | 0.421 | 100 |
| Ammonium sulfate precipitation (II) | 243 | 534 | 786 | 1.47 | 95 |
| DEAE-cellulose effluent (III) | 202 | 162 | 404 | 2.49 | 49 |
| Concentrate from XM-50 ultrafiltration (IV) | 3.5 | 25.6 | 320 | 12.5 | 39 |
| Sephadex G-150 (V) | 39 | 10.9 | 319 | 29.3 | 39 |

Purification steps II – V were carried out at 4° C.

For the large scale preparation of enzyme, *A. sialophilum* was grown at 30° C. for 24 hours in 20-1 jugs containing 10 L of TYE. After centrifugation, the cells were washed with 0.90% sterile NaCl, pretreated overnight in 10× M-9 and resuspended for 6 hours in 5 L of induction medium containing acid-treated bird's nest. The bacteria were removed by centrifugation (step I). Solid ammonium sulfate was added over a 6 hour period with mechanical stirring to 0.80 saturation, and the precipitate was dissolved in a minimal volume of 0.01 M citrate-phosphate buffer, pH 6.0 (step II). Solution was then submitted to ion-exchange chromatography on a column (2 × 80 cm) of DEAE-cellulose which had been equilibrated with the citrate-phosphate buffer. Under these conditions, neuraminidase was not absorbed but appeared in the effluent (step III). Further removal of low molecular weight material was effected by pressure filtration (nitrogen) through a Diaflow XM-50 filter (Amicon Apparatus Co.) (step IV). Additional purification was achieved by gel exclusion chromatography on a column of Sephadex G-150 (1.5 × 100 cm) which had been equilibrated with the citrate-phosphate buffer (step V). After salt removal by dialysis, the fractions containing neuraminidase activity were combined, lyophilized and resuspended in a minimum volume of 0.010 M citrate-phosphate buffer. The specific activity of the final preparation increased 71-fold to 29 units/mg protein, with an overall yield of 29%. Examination of this preparation by analytical disc gel electrophoresis either at acidic or basic pH revealed one predominant band (around 80%) with three minor protein (around 20%) contaminants. All of the neuraminidase activity in sliced gel sections was associated with the major band. In a separate analysis using specific staining with MPN, the enzyme was also localized coincident with the major protein. The amount of neuraminidase present in the induction filtrate (step 1) can be calculated from these data. Based on an estimated final specific activity of around 40 units/mg of protein for the homogeneous enzyme, and since the initial induction filtrate contained 206 units/l, this isolate can produce at least 5 mg of neuraminidase/l.

Enzyme characteristics. Enzyme activity increased linearly with concentration up to 0.28 mg/ml protein. The effect of pH on the activity was examined in citrate-phosphate buffer. A pH activity profile with Collocalia mucoid gave a broad optimum around 5–6. The $K_m$ values for Collocalia mucoid and N-acetylneuraminlactose were determined from the kinetic data given as inverse plots. These constants were found to be 2.08 mg/ml for Collocalia mucoid and $3.3 \times 10^{-3}$ M for N-acetylneuraminlactose. The following cations, whether included in the assay mixture or preincubated with the enzyme for 30 min at 37° C. and at concentrations between $10^{-3}$ M and $10^{-2}$ M, had no effect on neuraminidase activity: $Ca^{++}$, $Mg^{++}$, $Mn^{++}$ and $Co^{++}$. EDTA tested under the same conditions also had no effect on neuraminidase activity. The heat stability of *A. sialophilum* neuraminidase was shown to be maximal at 37° C. with sharp loss in activity after 50° C.

Preliminary experiments were carried out to determine the linkage specificity of the *A. sialophilum* neuraminidase. Colominic acid is a homopolymer of N-acetylneuraminic acid linked via an α-2,8-linkage, whereas N-acetylneuraminlactose is a mixture of the α-2,3- and α-2,6-isomers. Prolonged incubation of these substrates with neuraminidase resulted in the release of around 100% of the bound N-acetylneuraminic acid. From these experiments, it can be concluded that the *A. sialophilum* enzyme hydrolyzes either of the foregoing linkages. Additional experiments with separate, homogeneous isomers would be required to establish whether kinetic differences exist in the hydrolysis of these glycosidic linkages.

The molecular weight of *A. sialophilum* neuraminidase was determined by gel filtration on Sephadex G-150. A single symmetrical peak was obtained and a molecular weight of 87,000 daltons was calculated by extrapolation. It thus does not differ markedly in this property from a cluster of similar functional enzymes obtained from pathogenic microorganisms. This microorganism *A. sialophilum* exhibits non-fastidious aerobic growth, inducibility under defined conditions, production of extracellular activity with no detectable attendant glycohydrolases or N-acetylneuraminate pyruvate-lyase and formation of relatively large amounts of enzyme under standardized protocols.

The microorganism employed in the practices of this invention is identified as *Arthrobacter sialophilum* on the basis of its morphologic, staining, physiologic, and biochemical properties, and also in keeping with the substrates used for its isolation and enzymatic induction. The enzyme-producing organism in unstained preparations is a small, slightly curved non-motile rod which does not exhibit branching. The rod-shaped phase, initially gram variable, became Gram positive and underwent pleomorphic change to a spherical form on prolonged incubation in liquid medium. The colonies, initially colorless on solid media, became bright yellow with time except if maintained in the dark; a reaction characteristic of carotenoid pigments. It is halotolerant, surviving 18 hour exposure to 10% salt concentrations, can be repeatedly transferred on glucoseminimal medium, and, having been selected for at 37° C., grows up to 43° C. Its DNA base composition, 56.0 mol % GC, puts it at the lower end of those given in the literature for Arthrobacter isolates. This microorganism *A. sialophilum* exhibits non-fastidious aerobic growth, inducibility under defined conditions, production of extracellular activity with no detectable attendant glycohydrolases or N-actylneuraminate pyruvate-lyase and formation of relatively large amounts of enzyme under standarized protocols.

The design of the composition of the replacement induction medium, which eliminated carbon sources other than the complex inducer, precluded catabolite repression of enzyme induction, a phenomenon previously studied for several enzymes in the related *A. crystallopoietes*. Using commercially available $p$-$NO_2$-phenylglycosides and induction conditions which provided neuraminidase, no detectable $\beta$-galactosidase, $\beta$-glucosidase, $\beta$-glucosaminidase, $\alpha$- or $\beta$-fucosidase or $\alpha$-mannosidase activities could be detected, although $\alpha$-glucosidase was weakly present. These chromogenic glycosides reflect the carbohydrate compositional analysis of Collocalia mucoid (Kathan, R. H., and D. I. Weeks. 1969. Structure studies of Collocalia mucoid. I. Carbohydrate and amino acid composition. Arch. Biochem. Biophys. 134:572–576), but the findings indicate during the induction process that only terminal sialic acid-containing residues contributed to de novo enzyme synthesis. These observations contrast with the variety of glycohydrolases which were found in the response of *D. pneumoniae* to beef heart infusion broth.

The nature of the more potent inducer substance or substances present in "acid-treated" bird's nest is of interest. As indicated in Table 2, maximum induction was afforded by 1.5 hour treatment of bird's nest at 80° C. with 0.05N $H_2SO_4$. The data of Kathan and Weeks mentioned hereinabove concerning acid treatment of Collocalia mucoid with 0.1N $H_2SO_4$ for 50 as opposed to 60 minutes at this temperature provided evidence that the former conditions gave 4-0-acetyl-N-acetyl-neuraminic acid as the major sialic acid derivative liberated.

The general properties of the neuraminidase induced in this microorganism, e.g., apparent molecular weight of 87,000, pH optimum between 5–6, apparent $K_m$ of 3.3 $\times$ $10^{-3}$ M for N-acetylneuraminlactose, its insensitivity to $Ca^{++}$ ions and to EDTA, its linkage specificity and heat stability relate it to many other pathogenic bacterial neuraminidases (Balke, E., W. Scharmann, and R. Drzeniek. 1974. Die Bestimmung des Molekular gewichtes bakterieller Neuraminidasen mit Hilfe der Gelfiltration. Zentralbl. Bakteriol. Parasitenkd. Infektionskr. Hyg. Abt. 1 Orig. Reihe A 229:55–67; Drzeniek, R. 1972. Viral and bacterial neuraminidases, p. 35–75. In W. Arber, et al. (ed.), Curr. Topics in Microbiol. and Immunol., vol. 59. Springer Verlag, New York). The microorganism employed in the practices of this invention produces appreciably more neuraminidase than do alternative pathogenic or other diverse sources. Moreover, under the induction procedure detailed here, the enzyme is relatively homogeneous. The utilization of *A. sialophilum* for obtaining preparative quantites of neuraminidase, at minimal material expense and laboratory manipulations, is indicated.

A deposit of the above-described microorganism *Arthrobacter sialophilum* has been made with the American Type Culture Collection, Rockville, Md., U.S.A. and the deposit has been assigned ATCC No. 31253.

Following are the compositions of solutions useful in the practices of this invention. Table 5 gives the composition of tryptone-yeast extract (TYE) solution useful for the culturing or growth of the microorganism *A. sialophilum*.

TABLE 5

10 g of bacto-tryptone
5 g of yeast extract
liter of distilled water

Table 6 gives the compositions of various salt solutions, modified M-9 medium, useful in connection with the induction of neuraminidase from the microorganism *A. sialophilum*.

TABLE 6

| Component | Modified M-9 Medium | |
|---|---|---|
| | 2× | 10× |
| $Na_2HPO_4$ | 11.6 g | 58 g |
| $KH_2PO_4$ | 6.0 g | 30 g |
| NaCl | 1.0 g | 5.0 g |
| $NH_4Cl$ | 2.0 g | 10.0 g |
| $MgSO_4$ | 0.12 g | 0.60 g |
| $H_2O$ | 1 liter | 1 liter |

Table 7 sets forth steps in connection with the preparation of bird's nest as the inducing medium for the microorganism *A. sialophilum* for the production of neuraminidase therefrom.

TABLE 7

1. 300 g of Bird's Nest + 6 liter distilled water.
2. reflux for 6 hr at 100° C.
3. cool to room temperature.
4. filter.
5. add 1.39 ml of concentrated $H_2SO_4$ (36 N)/liter of filtrate.
6. heat at 80° C. for 1.5 hr.
7. cool to room temperature.
8. add around 300 ml of saturated $Ba(OH)_2$/liter of filtrate. Adjust pH to 7.0, if necessary.
9. centrifuge in Lourdes No. 1350 head at 5000 × g for 15 minutes.
10. dilute in half with distilled water.
11. sterilize by autoclaving at 121° C. for 30 minutes.

Table 8 sets forth various steps in connection with the growth of the microorganism *A. sialophilum* and the induction of neuraminidase therefrom including steps applicable for relatively large scale production of the microorganism and the enzyme.

TABLE 8

Cell Growth — Small Scale (50 ml)

1. Add 5.0 ml of sterile 0.9% NaCl to agar slant.
2. Take 2 ml from (1), and inoculate 50 ml TYE in 500 ml Erlenmeyer flask.
3. Grow at 30° C. for 16 hr. at 150 rpm.
4. Take 2 ml overnight culture (from 3) and inoculate 50 ml of TYE.
5. Grow at 30° C. for 10 hr at 150 rpm.
6. Centrifuge in 50 ml tubes at 12,000 g in SS 34 Sorvall rotor for 15 minutes.

7. Wash with 10 ml sterile 0.9% NaCl and centrifuge as above.
8. Resuspend cells in 5 ml of M-9 (B).

Enzyme Induction (Small Scale)

1. Take 4 ml of inducer
2. 0.5 ml of M-9 (B)
3. 0.5 ml of cells
4. Grow at 30° C. for 6 hr at 150 rpm.
5. Centrifuge as above.
6. Assay induction filtrate for neuraminidase.

Cell Growth — Large Scale (25 liter)

1. Add 5.0 ml of sterile 0.9% NaCl to agar slant. Take 2 ml from (1) and inoculate 50 ml TYE in 500 ml Erlenmeyer.
3. Grow for 16 hr at 30° C. at 150 rpm.
4. To 2 l Erlenmeyer each containing 500 ml TYE, add 20 ml of the 16 hour culture.
5. Grow for 24 hr at 30° C. at 150 rpm.
6. Inoculate 12.5 liter of TYE in 20 liter jug with 500 overnight culture (from 5).
7. Grow with aeration at 30° C. for 24 hr.
8. Harvest cells continuously with Sorvall Centrifuge at 19,000 × g at a flow rate around 125 ml/min.
9. Resuspend cells in 500 ml sterile 0.9% NaCl.
10. Centrifuge with Sorvall GSA rotor at 8,000 × g for 30 min.
11. Resuspend in 2.5 liter M-9 (B)
12. Store overnight at 4° C.

Enzyme Induction (Large Scale)

1. Take 10 liter of inducer
2. Inoculate with 2.5 liter of cells (from 11 B).
3. Grow for 6 hr at 30° C. in New Brunswick fermentor at an aeration rate of 2000 cc/min at 200 rpm.
4. Harvest by centrifugation with Sorvall GSA rotor at 8000 × g for 15 min.

Table 9 sets forth an assay procedure for neuraminidase.

TABLE 9

Assay Condition 1. 0.80 ml of Collocalia mucoid in 0.10 M citrate-phosphate buffer, pH 6.0.
2. Add 0.20 ml of enzyme.
3. Remove 0.20 ml aliquot at 0.5 for 10 minutes and assay for NANA according to the method of Warren, J. Biol. Chem. 234 1971–1975 "The Thiobarbituric Assay of Sialic Acids".

*All steps beyond (I) are carried out in the presence of $10^{-4}$ M phenylmethylsulfonyl fluoride.

Table 10 sets forth a preferred sequence of steps for the purification to homogeneity of neuraminidase derived from the microorganism A. sialophilum. *

TABLE 10

Purification of Neuraminidase from Arthrobacter sialophilum

| Preparation | Volume (ml) | Protein (mg) | Activity (units) | Specific Activity (units/mg protein) | Yield (%) |
|---|---|---|---|---|---|
| Induction filtrate (I) | 12,400 | 4489 | 3348 | 0.746 | 100 |
| Ammonium sulfate precipitation (II) | 430 | 484 | 3010 | 6.22 | 90 |

TABLE 10-continued

Purification of Neuraminidase from Arthrobacter sialophilum

| Preparation | Volume (ml) | Protein (mg) | Activity (units) | Specific Activity (units/mg protein) | Yield (%) |
|---|---|---|---|---|---|
| DEAE-cellulose effluent (III) | 540 | 224 | 2610 | 11.7 | 78 |
| Concentrate from XM-50 ultrafiltration (IV) | 3.3 | 79 | 2060 | 26.1 | 62 |
| Sephadex G-150 eluate (V) | 73 | 46 | 2497 | 54.3 | 75 |
| Concentrate from PM-10 ultrafiltration (VI) | 17 | 45.6 | 1384 | 30.0 | 41 |
| Ammonium sulfate crystallization (VII) 1st crystals | 5.0 | 8.2 | 490 | 59.8 | 15 |

It is indicated hereinabove that in accordance with the practices of this invention neuraminidase is derived from the microorganism A. sialophilum or variant or mutant or derivative thereof. A rough mutant thereof has been employed in accordance with the practices of this invention to produce neuraminidase. This rough mutant of A. sialophilum is especially attractive for the commercial production of neuraminidase because of the physical properties of the mutant in that the rough mutant is not slimy but, being rough, is more conveniently and easily handled and separated from the culture medium.

As will be apparent to those skilled in the art in the light of the foregoing disclosure, many modifications, alterations and substitutions are possible in the practice of this invention without departing from the spirit or scope thereof.

We claim:

1. A method for the preparation of a neuraminidase which comprises cultivating the microorganism Arthrobacter sialophilum ATCC 31253 or variant or derivative thereof in the presence of a neuraminidase-inducing substance therefor.

2. A method in accordance with claim 1 wherein the neuraminidase-inducing substance comprises a glycoprotein or low molecular weight glycopeptides.

3. A method in accordance with claim 1 wherein the neuraminidase-inducing substance comprises bird's nest, an edible regurgitated gelatinous material produced by the swiftlets of the genus Collocalia.

4. A method in accordance with claim 1 wherein said neuraminidase-inducing substance is acid-treated bird's nest.

5. A method in accordance with claim 1 wherein said neuraminidase-inducing substance comprises a hot water extract of bird's nest.

6. A method for the preparation of a neuraminidase which comprises cultivating the microorganism Arthrobacter sialophilum ATCC 31253 or variant or derivative thereof, harvesting the resulting produced microorganisms and inducing neuraminidase therefrom by contacting the harvested microorganisms with a neuraminidase-inducing substance therefor.

7. A method in accordance with claim 6 wherein said neuraminidase-inducing substance comprises a glycoprotein or glycopeptides.

8. A method in accordance with claim 6 wherein said neuraminidase-inducing substance comprises bird's nest.

9. A method in accordance with claim 6 wherein said neuraminidase-inducing substance comprises acid-treated bird's nest.

10. A method in accordance with claim 6 wherein said neuraminidase-inducing substance comprises an acid-treated hot water extract of bird's nest.

11. A method in accordance with claim 6 wherein the harvested microorganisms are contacted with an aqueous salt solution prior to inducing neuraminidase therefrom by contact with a neuraminidase-inducing substance.

12. A method in accordance with claim 11 wherein said aqueous salt solution comprises sodium chloride.

13. Extracellular neuraminidase derived from the microorganism *Arthrobacter sialophilum* ATCC 31253 or a neuraminidase-producing mutant or variant or derivative thereof, said neuraminidase having a molecular weight of about 87,000 daltons as measured by gel filtration chromatography, a pH optimum of 5–6, an apparent $K_m$ of about 2.08 mg/ml for Collocalia mucoid and $3.3 \times 10^{-3}$ for N-acetylneuraminlactose, being insensitive to both $Ca^{++}$ ions and EDTA and capable of hydrolyzing $(\alpha, 2\text{-}3)$, $(\alpha, 2\text{-}6)$ or $(\alpha, 2\text{-}8)$ linkages.

* * * * *